United States Patent
Bendale et al.

(10) Patent No.: US 9,045,808 B2
(45) Date of Patent: Jun. 2, 2015

(54) NANO GOLD AND PROCESS FOR PREPARATION

(71) Applicants: Yogesh N. Bendale, Karvenagar (IN); Vineeta Yogesh Bendale, Karvenegar (IN)

(72) Inventors: Yogesh N. Bendale, Karvenagar (IN); Vineeta Yogesh Bendale, Karvenegar (IN)

( * ) Notice: Subject to any disclaimer, the term of this patent is extended or adjusted under 35 U.S.C. 154(b) by 0 days.

(21) Appl. No.: 14/152,993

(22) Filed: Jan. 10, 2014

(65) Prior Publication Data

US 2014/0234439 A1    Aug. 21, 2014

Related U.S. Application Data

(63) Continuation of application No. PCT/IB2011/053097, filed on Jul. 12, 2011.

(51) Int. Cl.
| | | |
|---|---|---|
| *A01N 65/00* | (2009.01) | |
| *C22B 9/10* | (2006.01) | |
| *A61K 36/00* | (2006.01) | |
| *A61K 33/24* | (2006.01) | |
| *B22F 1/00* | (2006.01) | |
| *B22F 9/04* | (2006.01) | |
| *C22C 5/02* | (2006.01) | |
| *A61K 9/127* | (2006.01) | |
| *A61K 36/752* | (2006.01) | |
| *A61K 36/23* | (2006.01) | |
| *A61K 36/48* | (2006.01) | |
| *C22B 9/14* | (2006.01) | |
| *B82Y 30/00* | (2011.01) | |

(52) U.S. Cl.
CPC . *C22B 9/10* (2013.01); *A61K 36/00* (2013.01); *A61K 33/24* (2013.01); *B22F 1/0018* (2013.01); *B22F 9/04* (2013.01); *C22C 5/02* (2013.01); *A61K 9/1273* (2013.01); *A61K 36/752* (2013.01); *A61K 36/23* (2013.01); *A61K 36/48* (2013.01); *C22B 9/14* (2013.01); *B82Y 30/00* (2013.01)

(58) Field of Classification Search
CPC ..................................................... A61K 36/00
USPC ......................................................... 424/725
See application file for complete search history.

(56) References Cited

U.S. PATENT DOCUMENTS

2009/0041853 A1* 2/2009 Bendale .................. 424/545

* cited by examiner

*Primary Examiner* — Michael Meller
(74) *Attorney, Agent, or Firm* — Alfred F. Hoyte, Jr.

(57) ABSTRACT

This invention relates to bio synthesis of novel nano gold through environment friendly process with the aid of plant materials classified under the taxonomical genus *Dalbergia*, *Citrus*, *Ferula* and *Dolichos* or *Macrotyloma*. The present inventive product novel nano gold finds utility in, the treatment of humans and animals, nutraceutical, cosmeceutical and herbal composition, the field of technology including but not limited to nano technology, green technology and bio technology. The invention also relates to the use of plant materials in the purification and particle size reduction of metals.

3 Claims, No Drawings

NANO GOLD AND PROCESS FOR PREPARATION

CROSS REFERENCE TO RELATED APPLICATIONS

This application is a National Phase application of PCT Application No. PCT/IB2011/053097.

FIELD OF THE INVENTION

The field of the invention is metallurgy. More particularly, present invention is directed to a process for increasing the purity of gold to facilitate specific applications, and the product created by the process.

BACKGROUND OF THE INVENTION

Gold has been used therapeutically since ancient times. Orally administrable gold based products are known in traditional and alternative medicine. Further, gold based products obtained through various chemical reduction processes, ingestible and injectable, are also available for treatment of humans and animals. Gold salts obtained through chemical reduction are noticed to cause side effects due to toxicity thereby limiting its therapeutic application. Despite chemical purification, impurities are found on the surface of the gold particles, which causes various side effects upon administration in humans and animals. The toxicity of the gold based product causes side effects like nausea, vomiting, diarrhoea, dermatitis, haematological disorder. The main reason attributed to the toxicity is the change in oxidation state after administration and the carrier molecule. Orally administrable therapeutic gold products obtained through chemical reduction, for instance Auranofin or Ridaura, are noted to be less therapeutically effective than injectable gold salts.

With the advent of nano gold particles obtained through chemical reduction, e.g., by water arcing, electrochemical process etc., the therapeutic applicability of gold has improved. However, colloidal gold, obtained through chemical reduction processes results in stable and partially stable gold colloids or gold nano suspensions and are found to be less effective when orally administered. Nano gold products obtained through electrochemical processing have been found to have cleaner particle surfaces thereby increasing its efficacy in vivo and the particle size range from 8 nm to 100 nm as described in PCT/US2010/041427.

Gold based products known to have anti inflammatory properties and bacteriostatic effect are used in the treatment of rheumatoid arthritis, tuberculosis, cancer, asthma, HIV, Malaria etc. However, the toxicity and in vivo oxidation factor has caused its use in humans and animals to be restricted Further, gold nano particles, more robust and stable, are one of the most preferred nano materials in technological applications especially biomedical applications such as bio imaging.

The production of nano gold through various methods is known by those of skill in the art. Except, however, for process of production of 'swarna bhasma' there is no other known existent process to obtain nano gold through bio synthesis. The swarna bhasma, comprising of gold containing globular particles having an average size of 56 nm-57 nm, has been an integral part of traditional medicine in India. The traditional method comprises the steps of (1) purification with the aid of sesame oil (*Sesamum Indicum* Linn.), butter milk, cow's urine, sour gruel processed from *Oryza Sativa*, and extract of *Dolichos biflorous* Linn (2) special purification with the aid of hematite and rock salt and heating process (3) process of incineration by addition of mercury and sulphur in required proportion. The resultant product is a brownish red powder 'swarna bhasma'. (Brown C L et al, Gold Bulletin 2007).

The production and use of 'swarna bhasma' is further discussed in PCT/IN2008/000816, where the 'swarna bhasma' produced through traditional method is claimed in a method to perpetuate stemness in stem cell therapy. However, the process or the product discussed in that application is not similar to the present invention.

There exists the need for nano gold, stable and more robust, with higher mobility, adequate therapeutically effective particle size, and low toxicity to expand the applicability of gold metal.

OBJECT OF INVENTION

The object of the invention is the production of thermally stable and low toxicity nano gold of particle size ranging from 10 nm-1000 nm through bio synthesis for oral administration, with enhanced adsorption capacity, in treatment of humans and animals. The present invention is a merger between biotechnology and green technology for production of nano gold without toxic waste. The novel nano gold also finds application in various fields such as nano-technology, considering its stability, robust nature, particle size and low toxicity. Another object of the present invention is to establish an environment friendly process for the production of nano gold without toxic waste.

SUMMARY OF THE INVENTION

Novel particulate nano gold obtained through the present inventive process, bio synthesis, is therapeutically effective and non toxic when administered in specific dosages. The nano gold particulate produced by the inventive process is able to cross the blood-brain and placenta barrier due to their small particle size and faster mobility. The nano gold particles created by the process of the invention is also noted to induce apoptosis in cancer cells. The process is carried out with the aid of plant materials in a sequence of steps or phases.

Phase I of the process is that of purification of gold metal with the aid of *Dalbergia Sissoo* and *Dolichos Biflorous*. Phase II involves particle size reduction of the purified gold with the aid of *Citrus Acida* and *Ferula*. Phase III is of incineration for production of purified nano gold of size ranging from 10 nm-1000 nm.

The present invention is a novel bio synthesis process different from any prior methods including the process involved in production of 'swarna bhasma'. The plant materials used are different and the special purification process emphasised in the production of swarna bhasma with the aid of Mercury and Sulphur is not a part of this invention. Further, the temperature and the process of incineration differ in the present invention. The present invention uses *Dolichos Biflorus* independently of any other plant or organic material in the purification phase after the metallic gold is boiled with *Dalbergia Sissoo*. The traditional method involves the use of *Dolichos Biflorous* in conjuction with Cow's Urine, buttermilk etc.

The novel product obtained through novel process is pinkish brown or yellow in colour depending on the desired particle size. The novel product is thermally stable and also non toxic when administered in specific dosages.

This novel product has better therapeutic applicability especially in the treatment of cancer than any existent gold salts and nano gold particles. The novel product finds application in various other therapeutic treatment of humans and animals including but not limited to the treatment of rheumatoid arthritis, asthma etc. The novel nano gold also finds application as an anti-inflammatory, aphrodisiac and antioxidant. The application of the novel nano gold is also envisaged in herbal, cosmeceutical and nutraceutical products.

The administration can be carried out with suitable carriers such as honey, water or plant materials or minerals or combination thereof. The therapeutic effect and toxicity would vary with the type of carriers used for administration. The administration of the novel nano gold without suitable carriers is also envisaged in the present invention.

The applicability of the novel nano gold in the field of material science, biomedical application, biotechnology, nanotechnology, green technology and agriculture is anticipated in the present invention.

DETAILED DESCRIPTION OF THE INVENTION

The inventive process and product created thereby increase the applications of gold as a therapeutic. The product, novel nano gold, obtained through novel bio synthesis with the aid of plant materials, has increased adsorption capacity and is less toxic for oral administration. The novel product can be administered with or without suitable carriers or in conjunction with other plant materials or therapeutic complexes. The present invention also finds applicability in the field of nanotechnology, biotechnology, green technology and material science.

The present invention relates to the bio synthesis of nano gold particles through different steps of purification, trituration and incineration with the use of plant materials. The present invention deals with the process of obtaining nano gold through bio synthesis that is carried out in three phases i.e, the first phase is of bio purification of the metallic gold foils with the aid of extract of *Dalbergia Sissoo* and extract of *Dolichos biflorous* and the second phase is of trituration with other plant materials, such as *Citrus* and *Ferula*, for particle size reduction and third phase is of heating resulting in novel nano gold devoid of toxicity when administered in specific dosage, orally administrable, with higher adsorption capability. A key aspect of the present invention is the use of *Dalbergia Sissoo* in purification process of the metal and use of plant materials *Citrus* and *Ferula*, in the process of particle size reduction, which is not known in the prior art.

The particle size of the nano gold produced by the inventive process is also unknown in the prior art. The present inventive process produces novel nano gold of size 10 nm-1000 nm through bio-synthesis. The present invention not only is a novel bio process to produce nano gold particles but also includes the novel use of plant materials in metal purification and particle size reduction of metals. The use of plant materials taxonomically classified under Genus '*Dalbergia*' or in specific *Dalbergia Sissoo* or any other neoflavonoids having characteristics of the said compound in the purification process of the gold metal before particle size reduction is not known. The present invention provides for the use of mixture, in equal proportion by weight, of *Citrus Acida*, in liquid form, and *Ferula* in dry form, in particle size reduction of the gold metal purified through bio synthesis into nano gold of size 10 nm-1000 nm. Gold purified through any other method bringing same quality of the product of phase I is envisaged in use for particle size reduction with the aid of *Citrus Acida* and *Ferula*. Use of any plant material under taxonomical Genus '*Citrus*' and '*Ferula*' are anticipated in the present invention. Further, use of plant materials or chemical complexes with similar properties is anticipated in the said process of purification and particle size reduction of metals.

*Dolichos biflorous* is commonly used as an astringent, diuretic and tonic. The enzymes found in *Dolichos biflorous* have been identified as Urease, Allantoinase, Ribonuclease, Nicotinamide deaminase, b-n-acetylglucosaminidase, a and b galactosidase, a-mannosidase and b glucosidase. In the present invention it is used during the phase of purification after the metallic gold is boiled with *Dalbergia Sissoo*, which is a novel utility.

*Citrus Acida*, taxonomical classification Genus '*Citrus*' is commonly found in Asia. The juice of *Citrus Acida* contains Citric Acid, Mallic Acid, Phosphoric Acid and Salt. Medicinal properties of *Citrus Acida* are well known and it is also used as ingredient in food. The use of *Citrus Acida* in particle size reduction of metal is not known in the state of art. The present invention utilizes juice of *Citrus Acida* for particle size reduction of gold metal through bio synthesis. Plant under Genus '*Citrus*' such as Limonum, Medica, Aurantium, *Garcinia Pedunculata* or any other plant material containing citric acid and other contents found in *Citrus Acida* or compounds or chemical complexes that bring similar effect is anticipated in the present invention.

Plant materials under the Genus *Ferula* are known for their medicinal properties and are also used as food ingredient. *Ferula Narthex*, *Ferula Asafoetida* and *Ferula Foetida* are generally native to Iran and Afghanistan and has been widely used since ancient times in traditional medicine. However, the combination of *Ferula* with juice of *Citrus Acida* for particle size reduction of metal is not known in the state of art or traditional medicine. The present invention establishes a unique and non obvious use of plant materials under taxonomical Genus '*Ferula*' and '*Citrus*'.

The description of the process provided below is not to be considered limiting. One embodiment of present invention is the use of *Ferula Narthex* in conjunction with *Citrus Acida* in adequate proportion to reduce particle size of purified gold metal.

Phase I of the process involves bio purification of Gold metal, which is the first step in the process for production of nano gold. Gold metal, in the form of foils or otherwise, is heated, preferably at about 600 degrees centigrade, until red hot. The temperature of 600 degrees cannot be considered as limiting. Red hot gold metal is boiled in oil extract of *Dalbergia Sissoo* for several hours preferably minimum of seven (7) hours. The minimum time of seven (7) hours required for boiling cannot be considered limiting. The resultant product obtained after boiling with *Dalbergia Sissoo* is then boiled in extract of *Dolichos biflorus* for several hours, minimum of seven (7) hours but not limiting, to obtain metallic powder. The resultant product, i.e., metallic powder is put through the process of boiling with *Dalbergia Sissoo* and consequent boiling in extract of *Dolichos biflorous* several times in order to obtain organically purified gold through biosynthesis. The process is required to be repeated ten (10) times but the repetition of the process to the extent of ten times cannot be considered limiting being a natural process.

Phase II of novel process involves trituration. The product of Phase I is triturated with equal portion, by weight, of mixture of juice of *Citrus Acida* and *Ferula Narthex* in dry form, at temperature ranging from 22° C. to 45° C. until dry. The dry product obtained is further put through the process of trituration with mixture of *Citrus Acida* and *Ferula Narthex* repeatedly, minimum of ten (10) times, to reach the optimum finely divided desired particle size. The proportion of juice of *Citrus Acida* and dry *Ferula* in the mixture has to be equal by weight. The repetition of the process (10) times should not be considered as limiting. The desired particle size is the deciding factor of the number of repetition.

Phase III of the present inventive process involves incineration. The dry product after attaining its optimum particle size is exposed to high temperature ranging from 300° C. to 950° C. and cooled gradually until dry. The minimum temperature of exposure is preferably 300° C. This process of heating and cooling is repeated several times, minimum 10 times, until the dry product nano gold is obtained. The colour of the product varies from mild pinkish brown to yellow depending on the desired particle size. The number of times the process is repeated to obtain the product of desired particle size should not be considered as limiting being a natural process. Biomass, generally cow dung is used as fuel for the purpose of heating so as to ensure that the optimum range of heating and cooling is maintained. Use of biomass ensures that maximum optimal temperature is obtained prior to gradual cooling until dry product is obtained. This process of incineration is carried out in apparatus that provides uniform heating.

The pinkish brown or yellowish coloured fine dust of novel nano gold is biologically pure and particle size range from 10 nm to 1000 nm.

The administrable dosage of the novel nano gold normally ranges between 1 microgram to 100 mg per day. Dosage would vary depending on various factors hence the dosage form specified as 1microgram to 100 mg cannot be considered limiting. Specific dosage of the other minerals, which can be administered in combination with the novel nano gold, would normally range between 1microgram to 120 mg. The administrable dosage of the nano gold and the other minerals and plant materials vary on various factors, for instance the general health condition of the patient, age of the patient and in case of tumour, the kind of tumour and stage of the tumour. Hence the specified dosage cannot be considered as limiting in any manner.

Honey and water are the most commonly used suitable carriers but it shall not be considered as limiting as any other suitable carrier may be used for administration.

The pharmaceutical, nutraceutical, cosmeceutical or herbal composition or dosage form of the novel nano gold for administration can be in powder form, tablet, effervescent, fluid, gelatinous, granules or in any other palatable and administrable form.

What is claimed is:

1. A process for producing gold particles comprising the steps of:
   (a) subjecting a quantity of gold metal to heat until it becomes red hot to produce red hot gold;
   (b) boiling said red hot gold with an extract of Dalbergia Sissoo to form a mixture;
   (c) boiling of the mixture of step (b) with an extract of *Dolichos Biflorous* to form a product;
   (d) trituration of the product obtained from step (c) with a mixture of *Citrus Acida* and *Ferula Narthex* until dry to form a second product;
   (e) incineration of the second product obtained through step (d) by a method that subjects the second product of step (d) to gradual increases in temperature until the optimum maximum temperature is obtained to form a third product;
   (f) gradual cooling of the third product of step (e) until dry to form the gold particles.

2. The process of claim 1 wherein said gold particles are of a size between 10 nm and 1000 nm.

3. A gold particle produced according to the process of claim 1 which can be used therapeutically at a dosage of between 1 mcg and 100 mg daily in humans and animals.

* * * * *